United States Patent
Sonani

(10) Patent No.: US 7,559,693 B2
(45) Date of Patent: Jul. 14, 2009

(54) METHOD AND APPARATUS FOR X-RAY ALIGNMENT

(75) Inventor: Hiten Sonani, Naperville, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 49 days.

(21) Appl. No.: 11/950,882

(22) Filed: Dec. 5, 2007

(65) Prior Publication Data

US 2008/0144778 A1    Jun. 19, 2008

Related U.S. Application Data

(60) Provisional application No. 60/869,958, filed on Dec. 14, 2006.

(51) Int. Cl.
  *A61B 6/08* (2006.01)
(52) U.S. Cl. ..................................................... 378/206
(58) Field of Classification Search .................. 378/205, 378/206
  See application file for complete search history.

(56) References Cited

U.S. PATENT DOCUMENTS

| | | | |
|---|---|---|---|
| 4,167,675 A | 9/1979 | Stodberg et al. | |
| 4,502,147 A * | 2/1985 | Michaels | 378/206 |
| 4,521,905 A | 6/1985 | Hosokawa | |
| 5,316,014 A | 5/1994 | Livingston | |
| 5,438,991 A | 8/1995 | Yu et al. | |
| 5,708,696 A | 1/1998 | Kantor | |
| 5,835,562 A * | 11/1998 | Ramsdell et al. | 378/206 |
| 6,435,717 B1 * | 8/2002 | Kohler et al. | 378/206 |
| 6,694,169 B2 | 2/2004 | Kennedy et al. | |
| 6,779,920 B2 | 8/2004 | Stevanovic et al. | |
| 7,036,985 B2 | 5/2006 | Puente et al. | |
| 2006/0067483 A1* | 3/2006 | Hack et al. | 378/206 |

* cited by examiner

*Primary Examiner*—Chih-Cheng G Kao
(74) *Attorney, Agent, or Firm*—Alexander J. Burke

(57) ABSTRACT

An imaging system has an inventive light source coupled to its X-ray detector to project a visible light beam onto the patient so that the patient may be aligned with an area of exposure (e.g., the area which X-Rays from the emitter will contact). In some cases, the light beam is a rectangular beam which substantially indicates the area of exposure. The imaging system also has a motion detector to detect movement of the object, the X-Ray emitter, and the X-Ray detector. With the motion detector, the imaging system is automated to automatically turn the light source on whenever the patient or the imaging system (e.g., the table) moves. Similarly, the imaging system is automated to turn off the light source when X-Raying begins.

10 Claims, 5 Drawing Sheets

METHOD AND APPARATUS FOR X-RAY ALIGNMENT

This application claims the benefit of U.S. Provisional Application No. 60/869,958 filed Dec. 14, 2006 which is incorporated herein by reference.

BACKGROUND

An embodiment of the present invention relates generally to X-Ray systems and more particularly to alignment of X-Ray systems.

X-Ray technology has been employed extensively in medical imaging and other imaging fields. In certain X-Ray systems, such as angiography systems, patients may be exposed to X-Rays for long periods of time. These angiographic X-Ray systems generally position the X-Ray detector near the patient and/or a table on which the patient is placed and the patient and/or the table is aligned with the detector. The alignment is approximate and is based on a human interpretation of the position of the patient relative to the detector. That is, a health care provider generally makes an educated guess as to where the patient should be placed relative to the detector.

As such, initial positioning is often incorrect and the incorrect alignment is unrealized until the X-Ray system is started and the exact area of exposure is seen (e.g., at a display). This leads to increased exposure time for a patient as the patient must be re-aligned (e.g., re-positioned) and the new position must again be checked. Further, this leads to increased start-up and shut-down costs and wear on an X-Ray system when the X-Ray emitter is turned off during re-positioning of the patient. Accordingly, improved alignment systems and methods for X-Ray systems are required.

BRIEF SUMMARY OF THE INVENTION

An embodiment of the present invention includes an imaging system which may be aligned with a patient. The imaging system has a light source coupled to its X-ray detector to project a visible light beam onto the patient. The visible light beam illuminates an area to be X-Rayed (e.g., an area to be exposed). In some embodiments, the light beam may be a rectangular beam which substantially indicates the area of exposure (e.g., the area which X-Rays from the emitter will contact). In other embodiments, the light beam may be a solidly lit area, a cross-haired area, a cross-hatched area, et. The imaging system may also have a motion detector to detect movement of the object, the X-Ray emitter, and the X-Ray detector. With the motion detector, the imaging system can be automated to automatically turn the light source on whenever the patient or the imaging system (e.g., the table) moves. Similarly, the imaging system may be automated to turn off the light source when the X-Ray emitter is activated.

These and other advantages will be apparent to those of ordinary skill in the art by reference to the following detailed description and the accompanying drawings.

DETAILED DESCRIPTION

In an imaging system (e.g., a medical imaging system), a light is coupled to an X-Ray machine (e.g., at the X-Ray detector). The light projects a beam onto a patient which illuminates the area of the patient which is being exposed by X-Rays. That is, because the X-Ray emitter is directed through the patient toward the X-Ray detector, a light beam projected from the detector onto the patient indicates the area of the patient being X-Rayed (e.g., the area of exposure). The light beam may fully illuminate the area or exposure or may otherwise mark it (e.g., via an outline).

Figure 1:
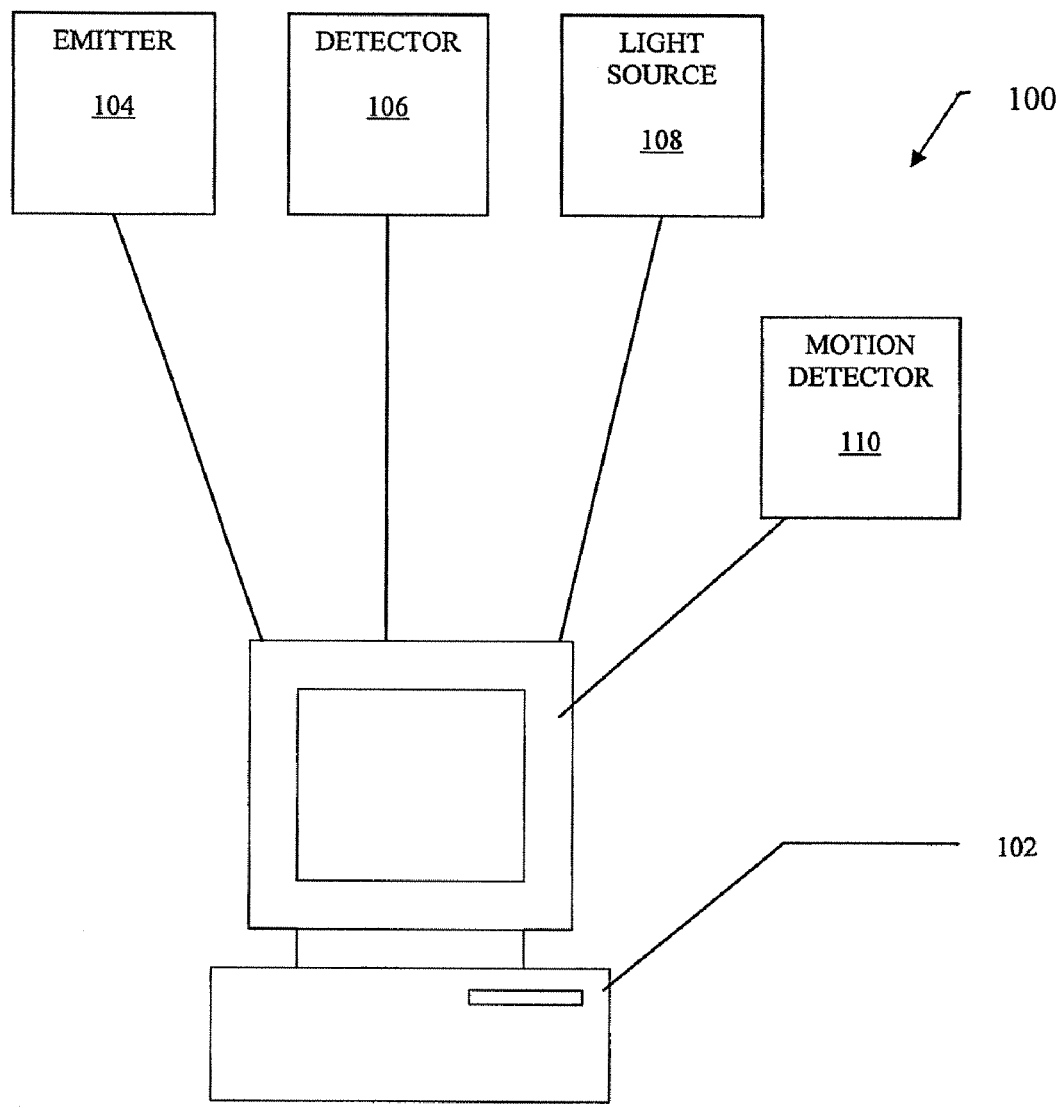
FIG. 1 is a schematic diagram of an X-Ray system according to an embodiment of the present invention.

FIG. 1 is a schematic diagram of an X-Ray system 100. X-Ray system 100 may have a controller (e.g., computer) 102. Controller 102 may be coupled to an X-Ray emitter 104 and X-Ray detector 106. The controller 102 may further be coupled to a light source 108 and a motion detector 110.

X-Ray emitter 104 and X-Ray detector 106 may be of any type as is known in the art. X-Ray emitter 104 may be capable of emitting X-Rays at a predetermined and/or adjustable strength. That is, the wavelength and/or frequency of the X-Rays may be adjusted using various amounts of energy. X-Ray detector 106 may include a camera and/or film (not shown), silicon based charge coupled devices for use in digital X-Rays, and/or any other implements used in radiography.

Light source 108 may be any appropriate light source capable of providing a visible light projection (e.g., a light beam). In some embodiments, light source 108 may comprise one or more lamps and/or one or more reflectors (e.g., parabolic reflectors) to direct a light beam onto an object. In the same and/or alternative embodiments, light source 108 may comprise one or more highly collimated beams of light, such as one or more lasers, similarly configured to direct visible light onto an object. In at least one embodiment, the light source 108 (e.g., the lamps and/or lasers) may be arranged in such a manner as to be capable of providing a particular pattern (e.g., a rectangle) of light on an object as will be discussed in further detail below with respect to FIGS. 2 and 3. Though generally discussed herein as a light source 108 projecting a light beam (e.g., light beam 210 in FIG. 2 below), it may be understood that light source 106 may project light in any manner consistent with the uses and methods described herein. For example, a fiber optic cable or other lighting aligned around an outside edge of detector 108 may be used in conjunction with reflectors to project the shape of the outer edge (e.g., a rectangular or circular pattern) onto an object even if the initial source of light is located in another place and the light is reflected through the optical fiber.

Motion detector 110 may be any device containing a physical mechanism and/or electronic sensor for quantifying motion indicative of a moving object within the field of view of the physical mechanism and/or electronic sensor. Motion detectors and/or sensors are well-known and will not be discussed in further detail herein except as used within the context of exemplary embodiments of the present invention.

Figure 2:
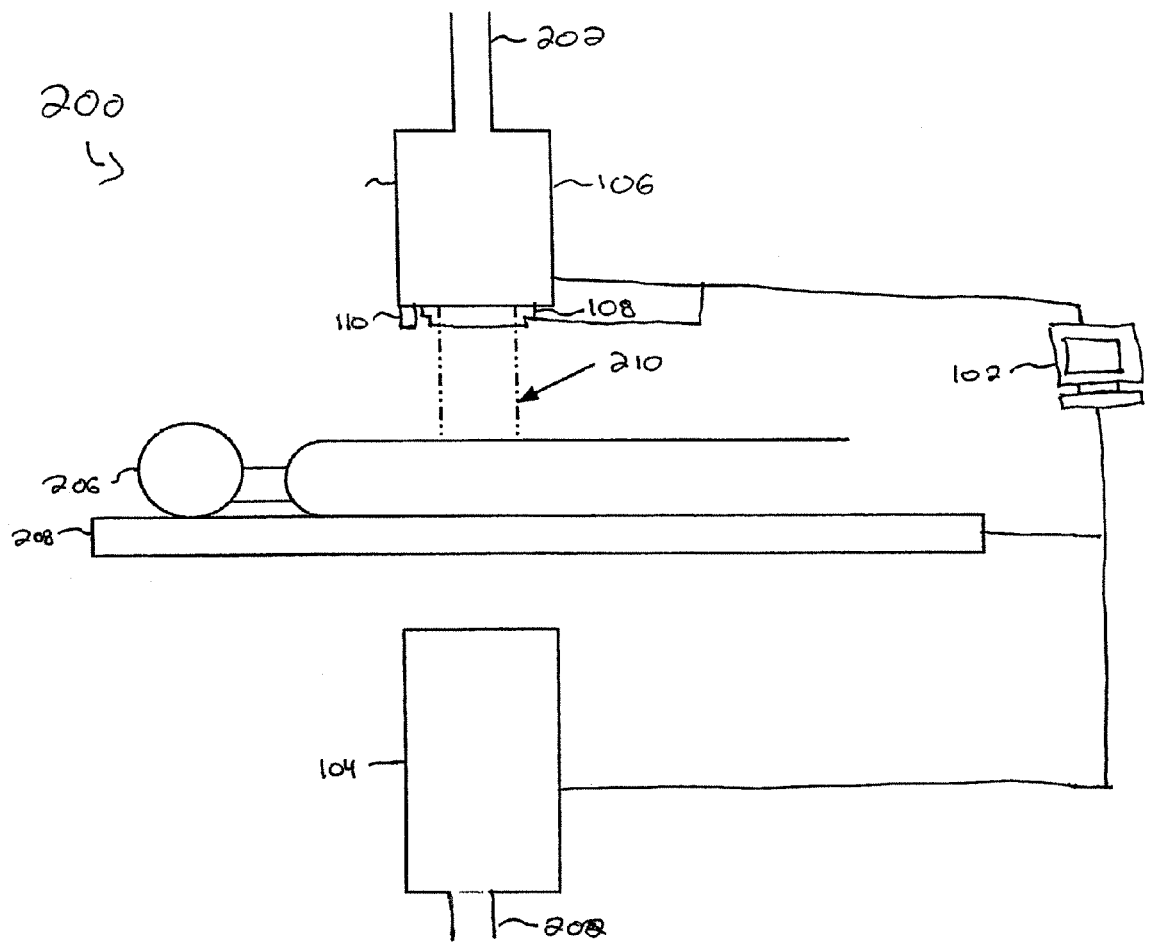
FIG. 2 is a diagram of an X-Ray machine according to an embodiment of the invention.

FIG. 2 is a diagram of an X-Ray machine 200 according to an exemplary embodiment of the present invention. X-Ray machine 200 may incorporate similar structures as described above with respect to FIG. 1. Accordingly, such structures will not be described again in detail except for their interrelation in X-Ray machine 200.

In at least one embodiment, X-Ray machine 200 may have a support arm 202. Support arm 202 may support emitter 104 and detector 106. In another embodiment, emitter 104 and/or detector 106 may each be supported separately (e.g., on other arms not shown in FIG. 2). Light source 108 may be mounted on and/or otherwise coupled to detector 106. In some embodiments, light source 108 may be incorporated into detector 106. Similarly, motion detector 110 may be mounted on and/or otherwise coupled to detector 106 and may be incorporated into detector 106. It is understood that light source 108 and/or motion detector 110 may be located elsewhere in X-Ray machine 200 and may be mounted on and/or coupled to another component (e.g., support arm 202).

Positioned between emitter 104 and detector 106 may be a support 204. Support 204 may be capable of supporting an object 308. Coupled to one or more of support arm 202, emitter 104, detector 106, light source 108, motion detector 110, and/or support 204 may be a controller 102.

Support arm 202 may be a c-arm as is known and may be maneuverable and/or positionable in any number of directions to facilitate X-Ray functions. Other arms and/or supports may be used. For example, a multi-jointed arm as is common in dental X-Ray machines may be used. In such embodiments, the support arm 202 may support the detector 106 and/or light source 108, but not emitter 104. In another exemplary embodiment, emitter 104 and/or detector 106 may be coupled to a track system for movement. In such embodiments, the light source 108 may be coupled on or about the detector 106 or may be located on another support. Other arrangements of the emitter 104, detector 106, and light source 108 may be used as is convenient.

Light source 108 may be coupled to the emitter 104, the detector 106, the support arm 202, or any other structure. In the particular embodiment depicted in FIG. 2, light source 108 may be supported proximal to the object 206, as shown. Light source 108 may be moveable and/or rotatable to facilitate projection of light. Such a light source 108 may be actionable by the motion detector 110 and may communicate therewith. That is, light source 108 may turn its associated light beam or beams on and/or off in response to signals from the motion detector 110. Though generally shown in FIG. 2 as a single light source 108, any number of projectors of light beams may be used. Herein, it may be understood that a light source may comprise multiple light sources and a light beam may comprise multiple light beams and the use of the singular form is merely for clarity and does not limit the present invention.

As shown in FIG. 2, light source 108 may project a visible light beam 210 onto object 206. Of course, if object 206 is not present, the light beam 210 may be projected onto support 204 or another destination. Since light beam 210 is visible, the object 206 is thus illuminated.

Support 204 may be a table or other means of supporting an object (e.g., a body or patient in medical applications) 308. In some embodiments, the support 204 may be controllable by the controller 102. That is, the controller 102 may send control signals to the support 204 and the support 204 may move (e.g., vertically, horizontally, and/or in tilt) in response to these signals.

Such signals may come in response to motion control signals from the motion detector 210. In at least one embodiment, the motion detector 210 may detect motion of the support 204 and/or the object 206 and transmit motion control signals to one or more of the controller 102, the emitter 104, the light source 108, and/or the support 204. These motion control signals may simply indicate motion of the object 206 and/or the support 204 or may provide directions such as turning on (e.g., automatically) the light beams of light source 108 whenever motion is detected, ceasing transmission of X-Rays from emitter 104 whenever motion is detected, and/or moving (e.g., rotating and/or moving vertically and/or horizontally) the support 204 whenever motion is detected to bring the original area of exposure back in line with the light beam 210 and/or emitter 104. Of course, any appropriate response to motion detected by the motion detector 110 may be indicated here and appropriate motion control signals may be transmitted as described above.

Figure 3:
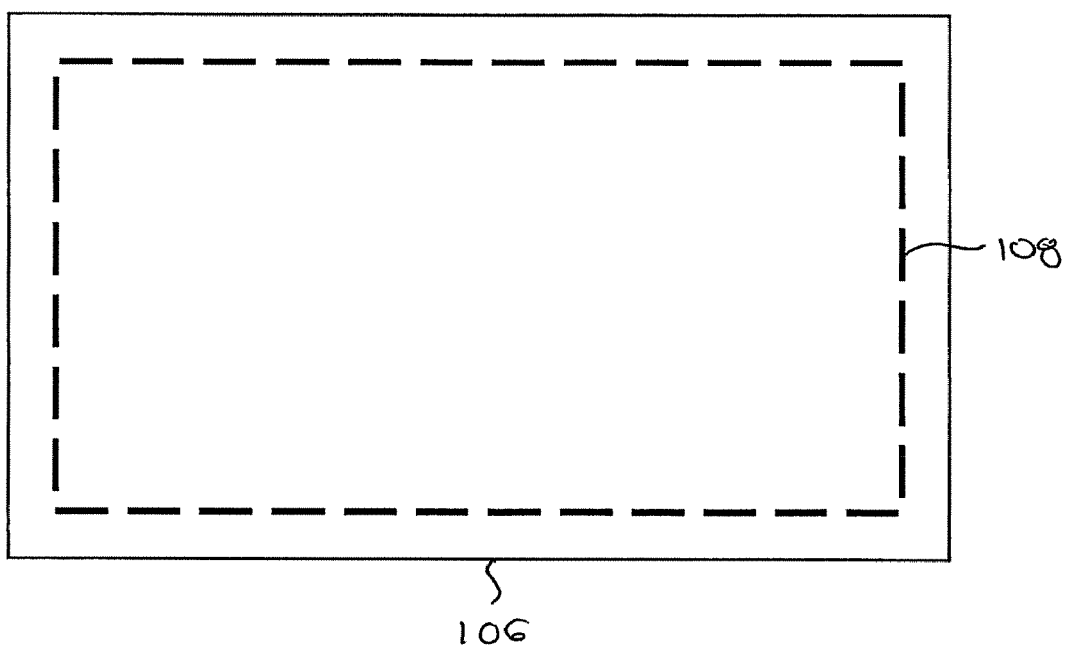
FIG. 3 depicts a bottom view of detector according to an embodiment of the invention.

FIG. 3 depicts a bottom view of detector 106. As described above with respect to FIGS. 1 and 2, light source 108 may be arranged along an outer edge of detector 106. In the schematic diagram of FIG. 3, light source 108 is depicted as a dashed line set in from the edge of the detector 106 for clarity. In some embodiments, the light source 108 may be arranged substantially co-incident with the outer edge of the bottom of detector 108. In other embodiments, the light source 108 may be arranged set-in from the edge of a housing surrounding the detector 106. Thus, in either embodiment, the light source 108 may be substantially co-incident with the area of exposure of the X-Ray machine. That is, the light source 108 may be arranged to substantially define the area in which X-Rays transmitted from the emitter 104 would contact the object 206 and/or the detector 108. Though depicted in FIG. 3 as a rectangle, the light source 108 may be co-incident with the edge of a detector or any shape and further need not follow the exact shape of the detector 106 edge. That is, in some embodiments, the light source 108 may be arranged in a different manner, such as in a pattern indicative of the area of exposure based on X-Rays transmitted from the emitter 104.

In the exemplary diagram of FIG. 3, each dash may be understood to be a part of light source 108 configured to direct a light beam (e.g., light beam 210) onto a patient (e.g., object 206). In this way, light source 108 may project a visible light beam onto a patient which illuminates substantially an outline of an area to be exposed by the X-Ray system 200 and indicates alignment of the area to be exposed on the patient. In some embodiments, light source 108 may be further arranged to project a shape other than an outline of the area to be exposed. For example, the light source 108 may be arranged to provide a cross-hair light beam 210 to indicate a center and/or outline of the area to be exposed. In another example, the light source 108 may be arranged to project a light beam 210 which is a substantially solid block of light on the object 206 indicating the area to be exposed. That is, the entire area of exposure may be illuminated. Other arrangements of light source 108 to project other illumination patterns may be used.

Figure 4:
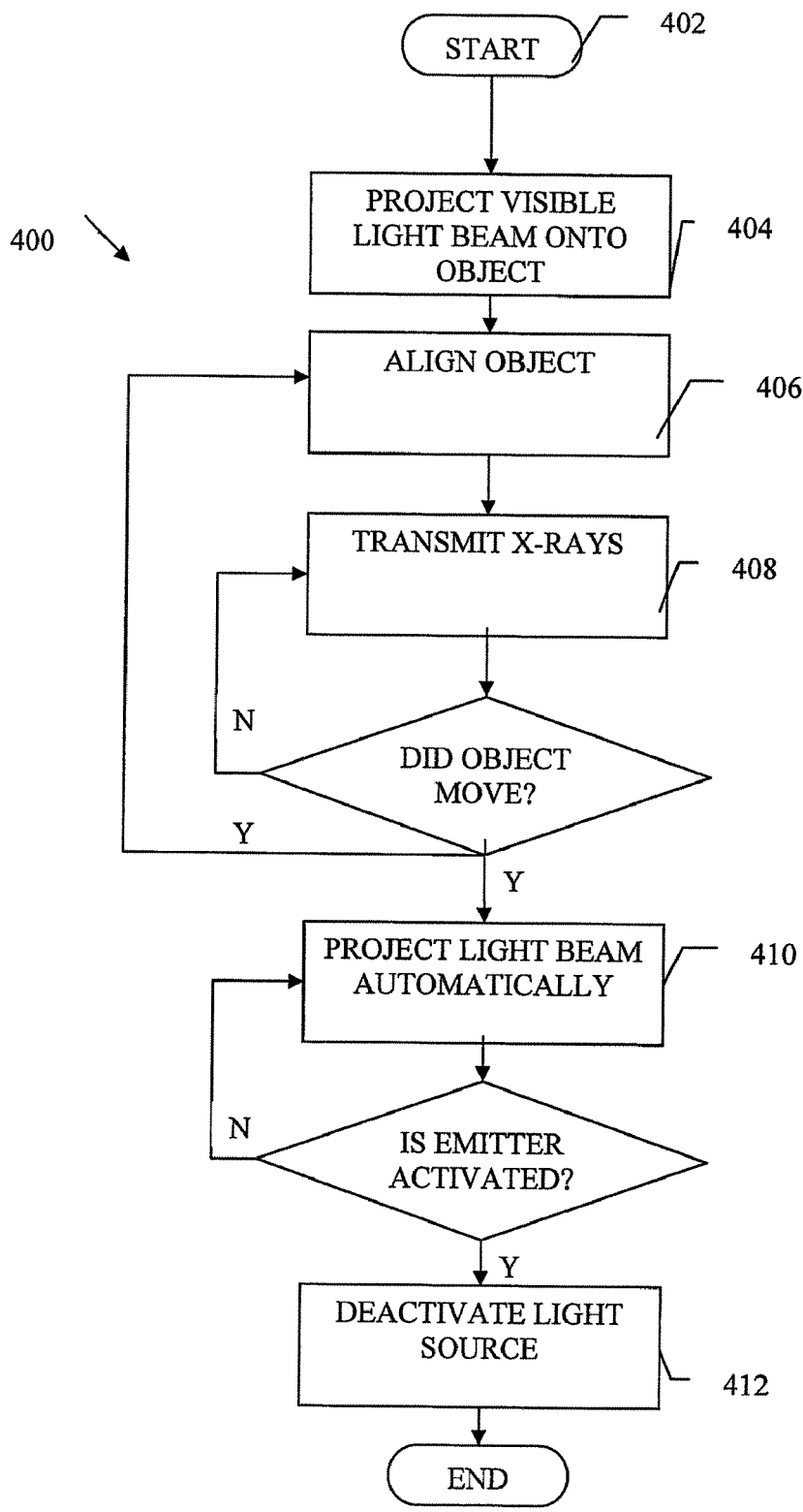
FIG. 4 shows a flowchart of a method for aligning an X-Ray system.

A method 400 for aligning an X-Ray system is depicted in FIG. 4. The method begins at step 402.

In step 404, a visible light beam is projected onto an object. The visible light beam may be a light beam 210 projected from light source 108 and may thus be projected from the direction of the detector 106, as shown in FIG. 2. The light beam 210 may illuminate an area to be exposed by the imaging system as described above with respect to FIGS. 2 and 3.

In step 406, the object is aligned with the imaging system based on the illuminated exposure area. The alignment may occur manually. That is, a user may move the emitter 104, detector 106, support 204, and/or object 206 to align the intended area of exposure with the light beam 210 so that when the X-Ray machine 200 is activated, the desired area is exposed. In an alternative embodiment, the emitter 104, detector 106, and/or support 204 may be moved based on control signals from controller 102. Based on the location of light beam 210 on the object 206 (e.g., as detected by motion detector 110 or another sensor), the controller 102 may determine the area which will be exposed as well as the intended area of exposure (e.g., as entered into controller 102 as discussed below with respect to FIG. 5) and may move one or more components of X-Ray machine 200 so that the desired area will be exposed.

In step 408, X-Rays are transmitted so as to expose substantially the area to be exposed. That is, emitter 104 may transmit X-Rays toward object 206 in a focused manner and the light beam 210 may substantially indicate the area of the object 206 which is being exposed to the X-Rays.

In step 410, the light beam is automatically projected onto the object when the object or the imaging system moves. During general operation of the X-Ray machine 200, such as during continuous transmission of X-Rays, the light source 108 may be deactivated (e.g., turned off). As described above, the motion detector 110 may detect motion of the object 206. Obviously, if the motion detector 110 is mounted to the X-Ray machine 200 (e.g., an imaging system), any movement of the X-Ray machine 200 could similarly be detected. When the object 206 and/or any portion of the X-Ray machine 200 moves, this may change the alignment of the X-Ray machine 200. That is, the emitter 104 may no longer be transmitting X-Rays toward the intended area of exposure.

When motion is detected by the motion detector 110, control signals may be sent by and/or to the controller 102 and/or the light source 108 to project the light beam 210 onto the object 206 (e.g., to turn the light source 108 on). In this way, the area being exposed may be seen by a user (e.g., a health care provider). Since the emitter 104 and the detector 106 are coupled via support arm 202, light source 108 coupled to detector 106 will continue to illuminate the area being exposed by the emitter 104.

Should realignment be necessary based on the re-illuminated area of exposure, the method may return control to method steps 404 and/or 406.

In step 412, the light beam is automatically deactivated when the X-Ray emitter is activated. During transmission of X-Rays by emitter 104, it may be unnecessary to continuously illuminate the area being exposed. When emitter 104 is activated, emitter 104 and/or controller 102 may send control signals to light source 108 indicating that light source 108 should turn off. Of course, should any movement be detected by motion detector 110, the method may return control to steps 404 and/or 410.

The method 400 ends at step 412.

Figure 5:
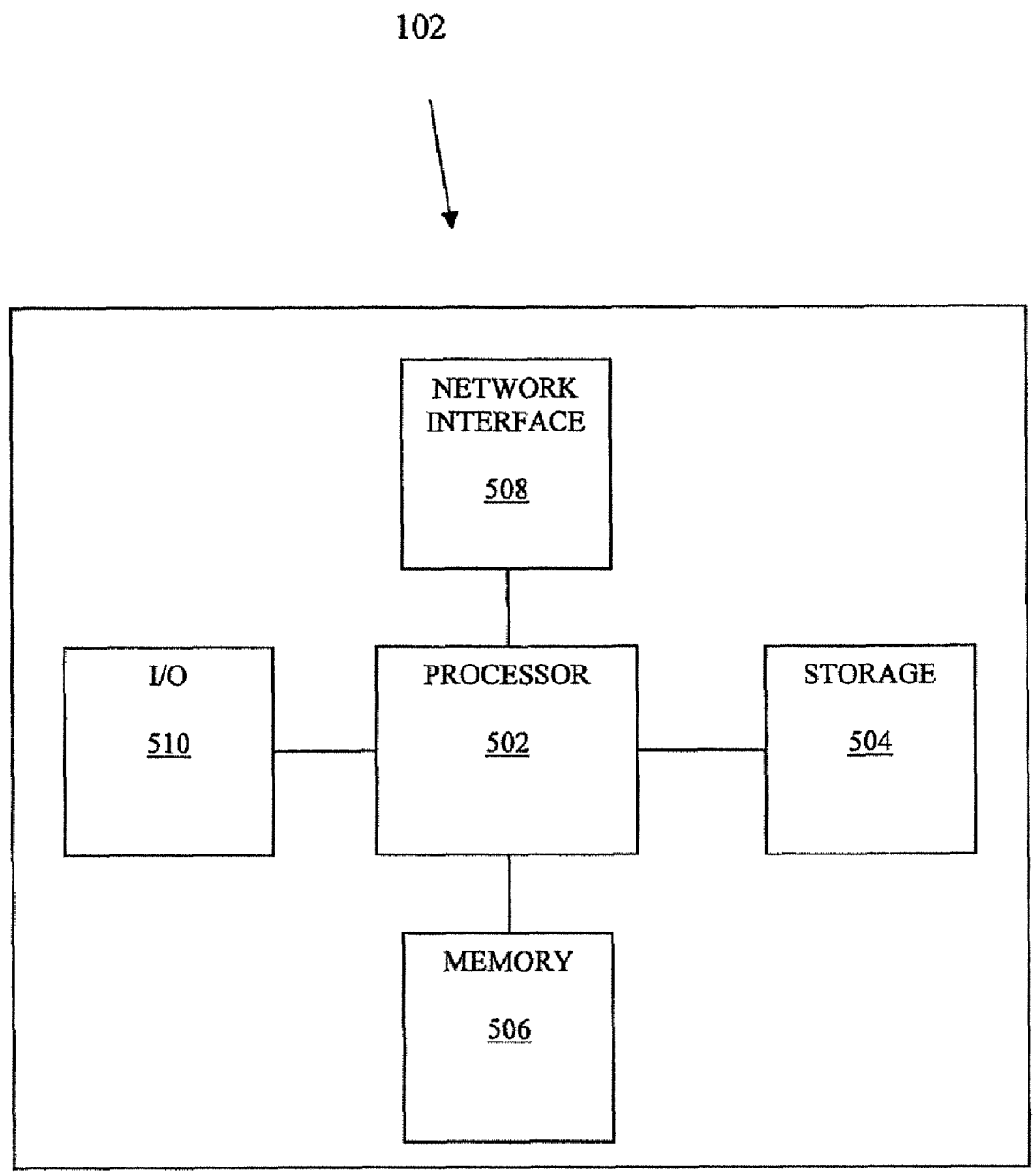
FIG. 5 is a detailed schematic drawing of a controller according to an embodiment of the invention.

FIG. 5 is a detailed schematic drawing of the controller 102 of FIG. 1. Controller 102 contains a processor 502 which controls the overall operation of the controller 102 by executing computer program instructions which define such operation. The computer program instructions may be stored in a storage device 504 (e.g., magnetic disk, database, etc.) and loaded into memory 406 when execution of the computer program instructions is desired. Thus, applications for performing the herein-described method steps, such as determining an area of exposure, activating and/or deactivating the light source 108 and/or the emitter 104, or aligning the intended area of exposure with the actual area of exposure, may be defined by the computer program instructions stored in the memory 506 and/or storage 504 and controlled by the processor 502 executing the computer program instructions. The controller 102 also includes one or more network interfaces 508 for communicating with other devices via a network. The controller 102 also includes other input/output devices 510 (e.g., display, keyboard, mouse, speakers, buttons, etc.) that enable user interaction with the controller 102 such as input of an intended area of exposure as described above with respect to method 400. One skilled in the art will recognize that an implementation of an actual controller could contain other components as well, and that the controller of FIGS. 1 and 5 is a high level representation of some of the components of such a controller for illustrative purposes.

Further, the controller 102, X-Ray emitter 104, and/or X-Ray detector 106 may be implemented on, may be coupled to, and/or may include any components or devices that are typically used by, or used in connection with, a computer or computer system. Controller 102 and/or processor 502 may include one or more central processing units, read only memory (ROM) devices and/or random access memory (RAM) devices.

According to some embodiments of the present invention, instructions of a program (e.g., controller software) may be read into memory 406, such as from a ROM device to a RAM device or from a LAN adapter to a RAM device. Execution of sequences of the instructions in the program may cause the controller 102, X-Ray emitter 104, and/or X-Ray detector 106 to perform one or more of the method steps described herein. In alternative embodiments, hard-wired circuitry or integrated circuits may be used in place of, or in combination with, software instructions for implementation of the processes of the present invention. Thus, embodiments of the present invention are not limited to any specific combination of hardware, firmware, and/or software. The memory 506 may store the software for the controller 102, which may be adapted to execute the software program and thereby operate in accordance with embodiments of the present invention and particularly in accordance with the methods described in detail below. However, it would be understood by one of ordinary skill in the art that the exemplary embodiments of the invention as described herein could be implemented in many different ways using a wide range of programming techniques as well as general purpose hardware sub-systems or dedicated controllers.

Such programs may be stored in a compressed, uncompiled and/or encrypted format. The programs furthermore may include program elements that may be generally useful, such as an operating system, a database management system and device drivers for allowing the controller to interface with computer peripheral devices, and other equipment/components. Appropriate general purpose program elements are known to those skilled in the art, and need not be described in detail herein.

The foregoing description discloses only particular embodiments of the invention; modifications of the above disclosed methods and apparatus which fall within the scope of exemplary embodiments of the invention will be readily apparent to those of ordinary skill in the art. For instance, it will be understood that, though discussed primarily as an alignment of an area to be exposed, the alignment is dependent upon multiple parts being in alignment and the light source 108 may similarly be used to indicate and/or facilitate alignment of any part of X-Ray system 200 within itself and/or with object 206. Similarly, other components may perform the functions of method 400 even when not explicitly discussed.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of exemplary aspects of the present invention and that various modifications may be implemented by those skilled in the art without departing from the scope and spirit of the invention. Those skilled in the art could implement various other feature combinations without departing from the scope and spirit of the invention.

The invention claimed is:

1. A method of aligning an imaging system comprising:
projecting a visible light beam from the direction of an X-Ray detector onto an object to illuminate an area to be exposed by the imaging system;
automatically projecting the light beam onto the object when the object or the imaging system moves; and
transmitting X-Rays so as to expose substantially the area to be exposed.

2. The method of claim 1 further comprising:
automatically deactivating the light beam when an X-Ray emitter is activated.

3. The method of claim 1 further comprising:
aligning the object with the imaging system based on the illuminated area.

4. The method of claim 1 further comprising:
aligning the imaging system with the object based on the illuminated area.

5. An imaging system comprising:
an X-Ray emitter;
an X-Ray detector;
a light source coupled to the X-ray detector and configured to project a visible light beam onto an object; and
a motion detector configured to detect movement of the object, the X-Ray emitter, and the X-Ray detector.

6. The imaging system of claim 5 wherein the light source comprises:
a light source configured to project a substantially rectangular light beam onto the object.

7. An apparatus for aligning an imaging system comprising:
means for projecting a visible light beam from the direction of an X-Ray detector onto an object to illuminate an area to be exposed by the imaging system;
means for automatically projecting the light beam onto the object when the object or the imaging system moves; and
means for transmitting X-Rays so as to expose substantially the area to be exposed.

8. The apparatus of claim 7 further comprising:
means for automatically deactivating the light beam when an X-Ray emitter is activated.

9. The apparatus of claim 7 further comprising:
means for aligning the object with the imaging system based on the illuminated area.

10. The apparatus of claim 7 further comprising:
means for aligning the imaging system with the object based on the illuminated area.

* * * * *